United States Patent [19]

Gouda

[11] Patent Number: 4,706,665
[45] Date of Patent: Nov. 17, 1987

[54] FRAME FOR STEREOTACTIC SURGERY

[76] Inventor: Kasim I. Gouda, 22 Baltimore St., Millis, Mass. 02054

[21] Appl. No.: 682,618

[22] Filed: Dec. 17, 1984

[51] Int. Cl.$^4$ ............................................. A61B 17/00
[52] U.S. Cl. .................................. 128/303 B; 604/116
[58] Field of Search .............. 128/303, 303 B; 60/594; 604/116

[56] References Cited

U.S. PATENT DOCUMENTS

| | | | |
|---|---|---|---|
| 4,341,220 | 7/1982 | Perry | 128/303 B |
| 4,350,159 | 9/1982 | Gouda | 128/303 B |
| 4,463,758 | 8/1984 | Patil et al. | 128/303 B |
| 4,465,069 | 8/1984 | Barbier | 128/303 B |
| 4,526,169 | 7/1985 | Narishige | 128/303 B |

Primary Examiner—John J. Wilson
Assistant Examiner—Wenceslao J. Contreras
Attorney, Agent, or Firm—Wolf, Greenfield & Sacks

[57] ABSTRACT

An improved stereotactic instrument for precise insertion of an electrode or a biopsy needle into the brain is designed for use with a computed tomographic (CT) scanner and does not require scanner software modification or complicated calculations to transfer the scanner coordinates of a desired brain location to the instrument. The instrument is based on a modified rectangular Gouda frame which can be temporarily attached to the CT scanner table by mounting plates that can be adjusted relative to one another until the frame is precisely aligned to the CT scanner zero reference plane. The frame is then affixed to the patient and after a plurality of CT scans are taken to establish the coordinates of the desired brain location, the patient and frame are detached from the CT table and moved to the operation room where coordinate arms and a electrode/needle holding arc are placed on the frame. The target coordinates obtained from the CT scanner can then be set directly on the coordinate arms of the frame.

28 Claims, 3 Drawing Figures

FRAME FOR STEREOTACTIC SURGERY

FIELD OF THE INVENTION

This invention relates to stereotactic instruments for use in treatment and biopsy of brain lesions and, in particular, to stereotactic instruments which are adapted for use with computed tomographic scanners.

DESCRIPTION OF THE PRIOR ART

A typical problem in neurosurgery of the brain is to precisely position a biopsy needle or an electrode to a point deep within the brain. It is often necessary to place the end of the needle or electrode within a small (often 1-2 mm) radius of a specific point within the brain to sample tissue or to perform functional neurosurgery. If such accuracy is not achieved, then improper diagnosis may result because a biopsy is taken of tissue surrounding a lesion. Alternatively, serious damage may be caused to the brain tissue. The positioning problem is complicated because measurements must be made in three dimensions. Often, the desired point is not accessible by open cranial surgery and thus it must be located indirectly by using X-rays or other scanning equipment to locate certain characteristic areas of the brain and then by determining the location of the desired point relative to these characteristic areas.

After the desired point is located, apparatus known as a stereotactic surgical instrument is used to assist the surgeon in mechanically guiding the needle or electrode to the proper position. Stereotactic instruments have been used on experimental animals as long ago as 1908 and until recently, such instruments relied mainly on the use of X-rays to detect the position of known areas of the brain, such as the anterior and posterior commissures of the third ventricle. The instruments were designed so that portions of the instruments known as "markers" appeared on the X-ray image used to locate the known structures of the brain. Once the location of the brain structures was established relative to the marker locations, other points in the brain could be related to the marker positions by means of brain anatomy charts. A needle holder was then precisely positioned with respect to the marker locations by calculating its position using the brain anatomy charts and the known brain area positions and used to guide the needle or electrode to the desired brain location.

Unfortunately, the anterior and posterior commissures in the third ventricle of the brain are not opaque to X-rays and thus in order to use such stereotactic instruments it was necessary to introduce radio-opaque material into these portions of the brain so that sufficient contrast could be obtained on the X-ray film to identify their location. This procedure required two burr holes to be drilled in the skull. In addition, the X-rays used to form the images of the brain structures were subject to diffraction effects which either limited the accuracy of the procedure or required complicated calculations to compensate for such effects.

Recently, computed tomographic (CT) scanners have been extensively used. These devices rely on a moving X-ray source which generates low-level X-rays that penetrate the subject from different angles. The intensity of the radiation passing through and scattered by the subject is detected and the intensity pattern produced by the moving source is analyzed by a computer. The computer constructs a composite image of a thin cross-section or "slice" of the subject on which is superimposed a "grid" of coordinates. The computer can provide and display a direct computation of the "coordinate" values of any location on the grid for each slice and can indicate location of the slice relative to an initial reference slice or plane.

The use of such scanners is advantageous over prior art devices using X-rays because the scanners can directly identify portions of the brain such as the anterior and posterior commissures. Accordingly, many existing stereotactic instruments have been modified to allow their direct use with a CT scanner. However, these instruments typically require modifications in the software of the CT scanner or complicated calculations to convert the coordinate values produced by the scanner to mechanical settings which can be used to adjust the devices to place a needle or electrode at a desired brain location. Still other instruments require that all surgical operations be performed in the CT scanner room and some arrangements are so elaborate that they require sophisticated computer knowledge to operate.

More recently a stereotactic instrument known as the "Gouda Frame" was modified for use with a CT scanner. Such modification is described in an article entitled "Modification of the Gouda Frame to Allow Stereotactic Biopsy of the Brain Using the GE 8800 Computed Tomographic Scanner", K. Gouda, S. Freidberg, C. Larsen, R. Baker, and M. Silverman, *Neurosurgery*, V. 13, no. 2, August 1983. With this modified instrument it was possible to directly use the scanner-generated coordinate values of a particular area in the brain to mechanically adjust the frame.

There remained problems with this latter modified instrument, in that it was difficult to align the modified frame properly with the initial reference plane of the CT scanner. Any misalignment between the frame and the reference plane of the scanner resulted in inaccuracy of the final adjustments. In addition, the Gouda Frame contained a complicated mechanical adjustment arrangement which, due to mechanical tolerances, made adjustment of the frame to the required accuracy difficult.

Accordingly, it is an object of the present invention to provide a stereotactic neurosurgical instrument which is directly compatible with a CT scanner.

It is another object of the present invention, to provide a stereotactic instrument which is simple to operate and is not subject to mechanical tolerances which upset the accuracy of the instrument.

It is yet another object of the present invention to provide a stereotactic instrument which can be easily and quickly aligned to the reference plane of the CT scanner.

It is still a further object of the present invention to provide a stereotactic instrument which does not require a surgical operation to be performed in the CT scanner room.

SUMMARY OF THE INVENTION

The foregoing objects are achieved and the foregoing problems are solved in one illustrative embodiment of the invention in which a modified Gouda Frame is provided with adjustable adapter plates for attachment to the CT scanner table and with a simplified coordinate adjustment mechanism. The adjustable adapter plates can be precisely positioned with respect to each other in two planes by means of adjustment screws and can be rotated with respect to one another. One plate is fastened to the CT scanner table and the other to the modified frame so that the relative alignment of the two members can be adjusted prior to performing a surgical operation so that the frame is exactly perpendicular to the scanner table.

In particular, the modified Gouda Frame consists of a rectangular metal frame which is affixed to the skull by means of four pins in a known manner. At the center of each side of the frame is located a plastic alignment post on which is etched a cross-hair marking. A 1-mm lead shot marker is embedded in the post at the center of the cross-hair marking.

Prior to performing an operation, the frame is attached to the CT scanner table by the adapter plates. The CT scanner laser beams are visually aligned with the cross-hairs on the alignment posts and an initial lateral scout scan is taken with the CT scanner showing the scanner reference plane. The screw adjustments on the adaptor plates can then be manipulated until the zero reference line of the scanner reference plane passes through the images of the four marker shots. An axial scan is then taken and the frame is rotated until the images of the shots align with the "X" and "Y" coordinate lines of the scanner image. At this point the adapter plate settings are locked, thus insuring that the mechanical coordinates determined by the frame will be correspond directly to the coordinates generated by the scanner.

To perform a surgical operation, the frame is affixed to the head of the patient in the usual manner. The alignment posts are placed on the frame and lateral and axial scans are taken in the scanner reference plane to insure that the frame alignment is correct. The alignment posts are then removed from the frame and additional CT scans or "slices" are taken. The patient and the frame are then detached from the CT table and moved to the operating room. A set of manually-adjustable, graduated coordinate arms are then mechanically attached to the frame. The graduated markings on the arms are such that the target coordinates obtained from any slice of the CT scan can be simply, manually set directly on the arms. Because the frame has been pre-aligned to the CT table there need be no corrections for misalignments.

Once the coordinates obtained from the scan have been set, an arc is fitted to the measurement arms which guides the biopsy needle or electrode. The needle is contained in a precision holder and can be preset a predetermined distance to the target area location by means of a simple calibration rod. The position of the needle on the arc can be moved and the arc can be rotated in a circular path so that the needle can be introduced into the skull through an existing burr hole. When the needle has been extended the predetermined distance, the tip of the needle is fixed on the target area.

DETAILED DESCRIPTION OF THE PREFERRED EMBODIMENT

Figure 1:
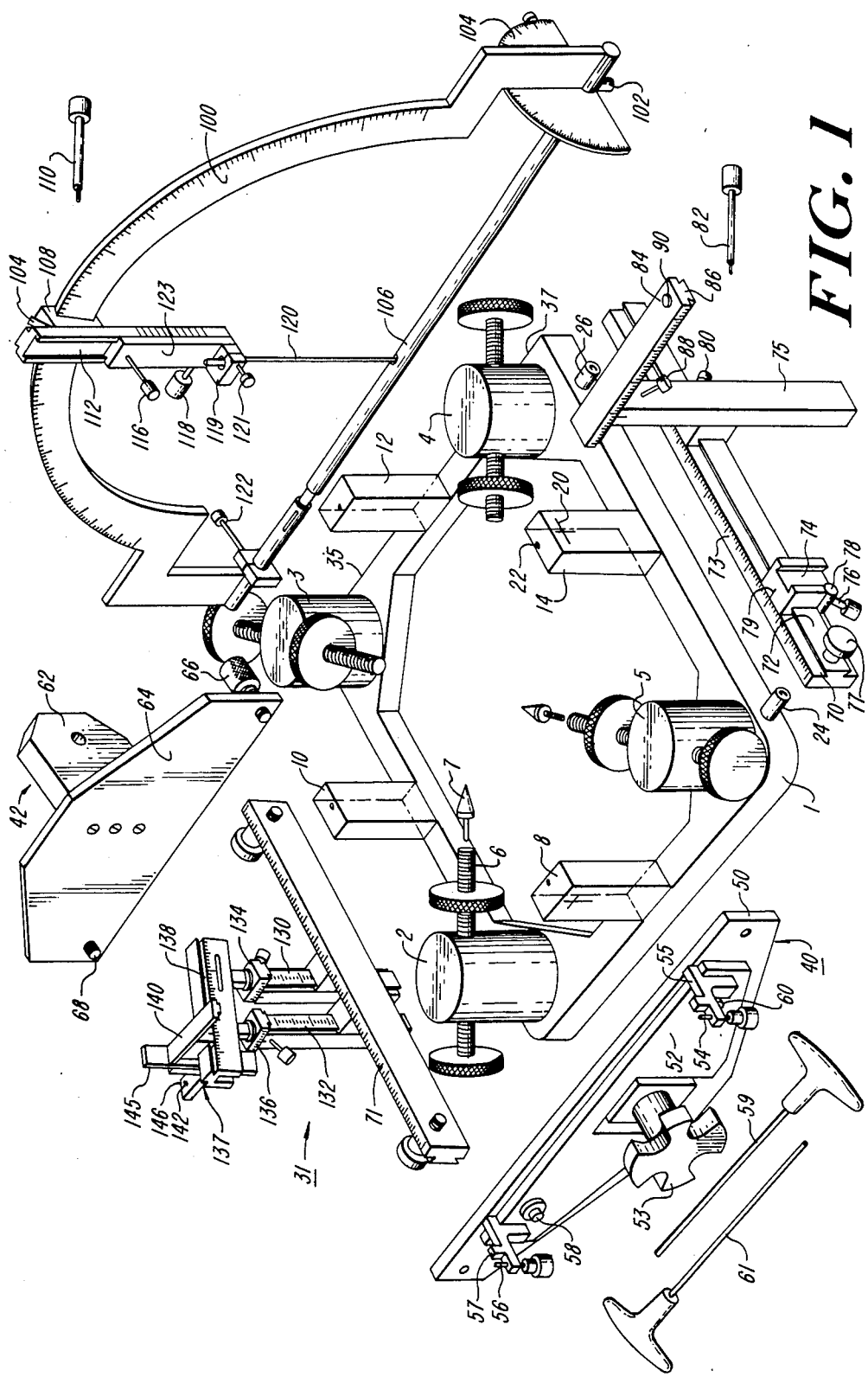
FIG. 1 is a perspective view of the stereotactic frame with an array of components used during the scanning and during subsequent operations.

The modified Gouda frame consists of a rectangular metal frame 1 which may be comprised of any suitable metal (such as aluminum) that is light and rigid. Attached to the four corners of the frame are blocks 2-5, respectively. Blocks 2-5 are comprised of a radio-translucent material, such as a plastic material. A material suitable for use with the illustrative embodiment is a plastic material known as Lexan manufactured by the E. I. Dupont De Nemours, Inc.

Blocks 2-5 are used to support the screw mechanisms which fasten the frame to the patient's skull. In particular, each block, such as block 2, is provided with a thumbscrew 6 which is also comprised of a radio-translucent material, for example, Lexan. Adjustment screw 6 is fitted with a stainless-steel pin 7 which affixes the frame to the patient's skull. The other blocks 3-5 are similarly fitted with adjustable screws and pins.

Frame 1 is also provided with four alignment posts 8-14. Each of the alignment posts, such as post 14, is provided on its outer surface with a cross-hair marking 20. Embedded in the center of the block, directly opposite the cross-hair marking is a 1-mm lead shot. Each of the other blocks 8-12 is also provided with a similar cross-hair marking on its outer surface and a lead shot in the corresponding center location. Alignment posts 8-14 are initially positioned at the center of each side of the frame and are used, as will hereinafter be described, to position the frame in the zero reference plane of the CT scanner.

Frame 1 is also provided with a plurality of studs (of which studs 24 and 26 are shown) for attaching the graduated measurement arm mechanisms 30 and 31, as will hereinafter be described.

Frame 1 is also provided with tapped holes at locations 35 and 37 to which adaptors 40 and 42 can be connected for attachment of the frame to the CT scanner table and to an appropriate headrest, respectively.

In particular, adaptor 40 is comprised of a backplate 50 which is fastened to the CT scanner table by means of a threaded screw that is rotated by knob 53. A typical CT scanner has a moveable table on which the patient lies and which rests on a fixed base. A gantry containing the scanning mechanism is positioned in a fixed location relative to the base and the table can be moved precisely with respect to the base to position the patient relative to the scanning mechanism. As will be hereinafter described, the screw from the frame 1 fits into a threaded hole located in the CT scanner table and thus the patient and frame move as a unit. A conventional example of a CT scanner which can be used with the illustrative embodiment is a Model 8800 CT scanner manufactured by the General Electric Company, Medical Systems Division, Milwaukee, Wis. 53201.

Frontplate 52 is attached to backplate 50 by means of screw adjustments 58 and 60. Frontplate 52 is, in turn, attached to frame 1 by means of brackets, 55 and 57, and attaching screws, 54 and 56. Attaching screws 54 and 56 fit into holes 35 and 37, respectively.

In accordance with the invention, prior to performing a series of scans on a patient, the relative alignment of the frame 1 and the CT scanner table can be adjusted by manipulating the connection between front plate 52 and back plate 50 so that the marker shots in the alignment markers 8-14 fall precisely in the zero reference plane of the scanner and align with the scanners internal coordinate system. Later, when the frame is affixed to the patient, it provides a fixed set of mechanical reference coordinates which directly correspond to the internal scanner coordinates because of the initial alignment. More specifically, as will hereinafter be described in detail, after backplate 50 has been attached to the CT scanner table and frame 1 has been attached to frontplate 52, the relative alignment of the two plates can be changed by manipulating adjustment screws 58 and 60 with Allen wrenches, 59 or 61. Since the adjustments 58 and 60 are independent, the relative alignment can be adjusted in two axes.

After the CT scans have been performed, adaptor 40 is removed from frame 1 and adaptor 42 is attached to frame 1 by means of screws 66 and 68 which fit into holes 35 and 37, respectively. Screws 66 and 68 pass through plate 64 which is, in turn, attached to member 42. Member 42 is attached in conventional manner to a known supporting arrangement, such as a "Mayfield" headrest, to immobilize the patient's head for a subsequent surgical operation.

Figure 2:
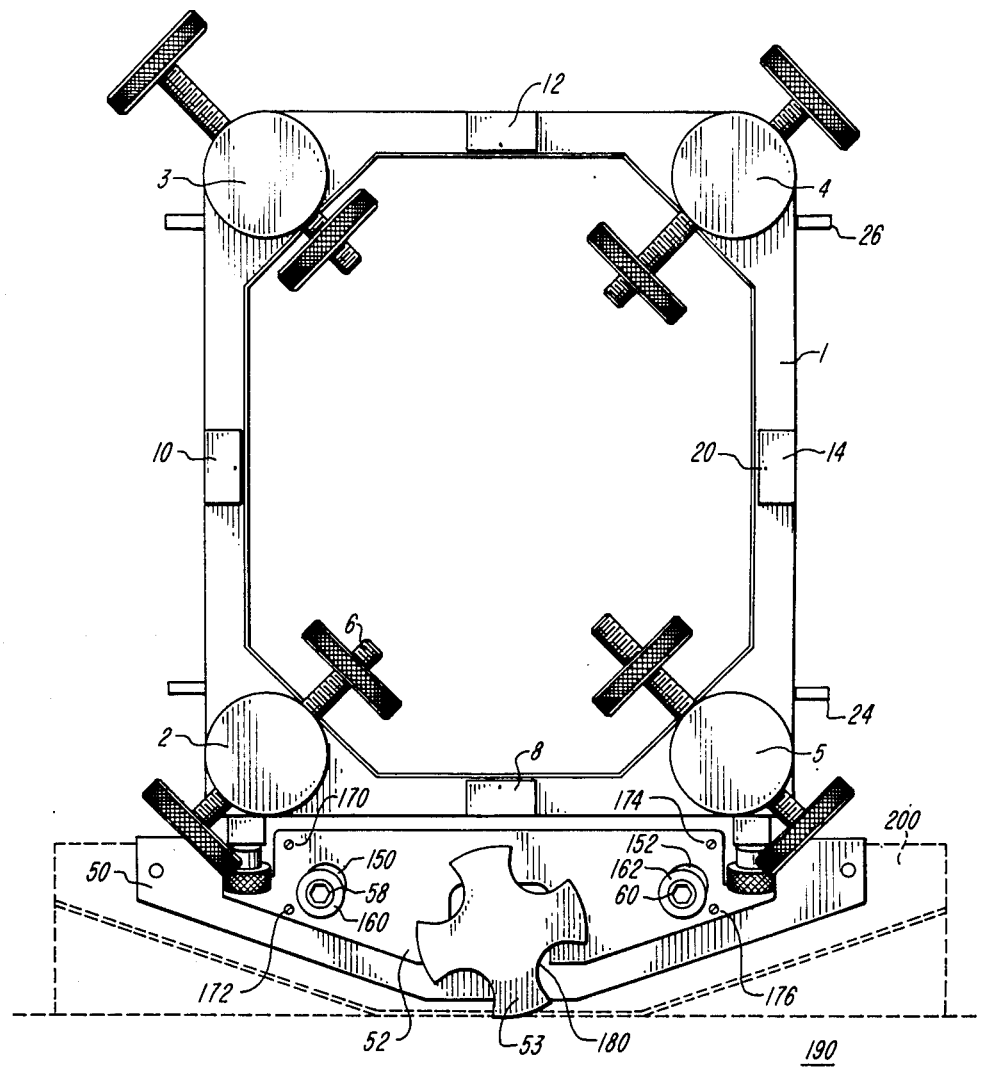
FIG. 2 is an enlarged top view of the modified frame showing the adaptor plates which attach the frame to the CT scanner table.
Figure 3:
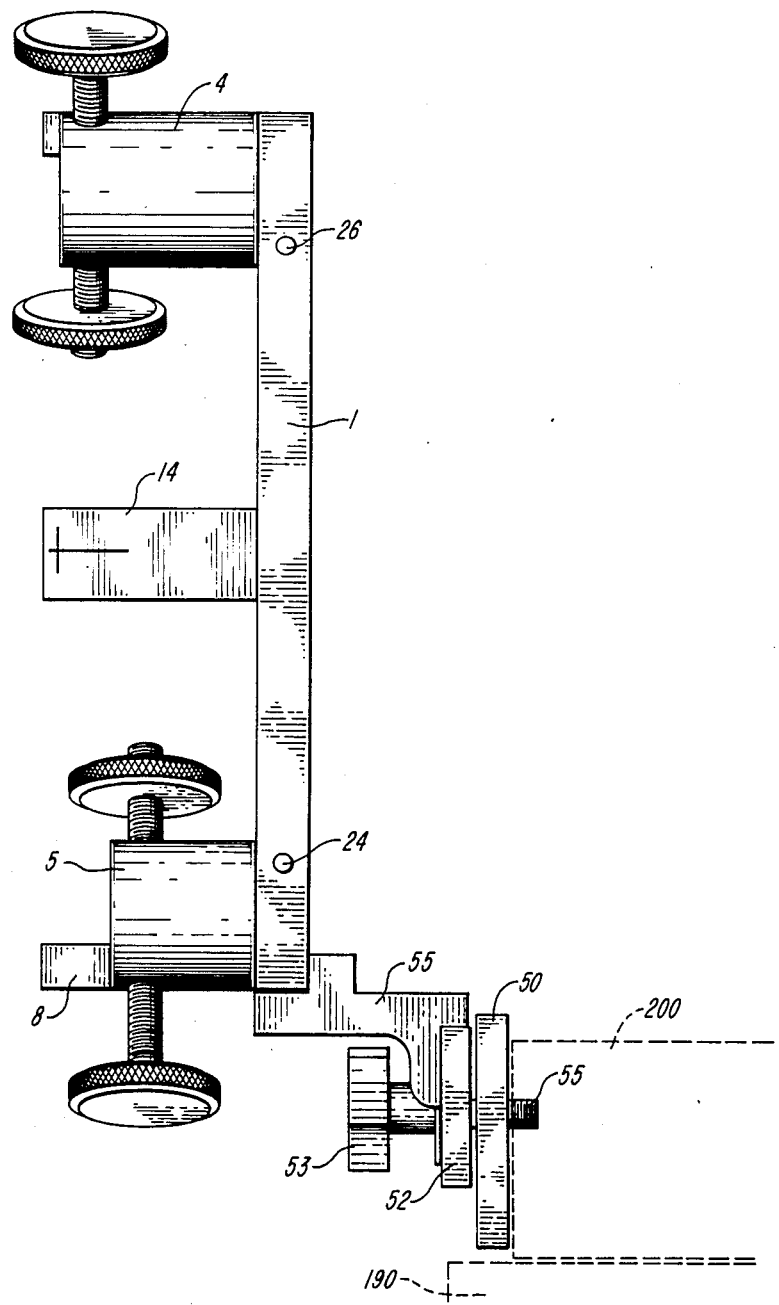
FIG. 3 is a side view of the frame as attached to the CT scanner table by means of the adapter plates.

FIGS. 2 and 3 of the drawing show a top view and a side view, respectively, of frame 1 as it is mounted on the end of the CT scanner table. FIGS. 2 and 3 also show a more detailed view of the adjustable mounting plates which allow frame 1 to be adjusted relative to CT scanner table 200. In particular, the adjustable plates consists of back plate 50 which is fastened firmly to the movable CT table 200 by means of a thumbwheel 53. As shown in FIG. 3, this thumbwheel drives screw 55 which engages a threaded hole in the end of scanner table 200. Table 200, in turn, rests on base 190.

As previously mentioned, frame 1 is attached by brackets 55 and 57 to front plate 52. Plate 52 has a clearance hole 180 cut through it so that it does not interfere with the operation of the thumb wheel 53. Plate 52 is mechanically fastened to plate 50 by means of two screws, 58 and 60. These screws pass through oversize holes 150 and 152 in plate 52 and thread into the back plate 50. The heads of screws 58 and 60 bear against flat washers 160 and 162 which, in turn, bear against plate 52. Thus, when screws 58 and 60 are loosened, plate 52 may be moved relative to plate 50 within the limits of the oversized holes 150 and 152. When screws 58 and 60 are tightened, plates 50 and 52 are held in a fixed relationship.

The relative alignment of plates 52 and 50 is controlled by alignment set screws 170-176. These screws are threaded through plate 52 and bear against plate 50. By loosening attachment screws 58 and 60 and then by adjusting one or more adjustment screws 170-176, the plane of plate 52 (and thus of the stereotactic frame 1) can be adjusted relative to the plane of plate 50 (and thus of table 200). Once the proper alignment has been made, screws 58 and 60 are tightened to lock the plates into position.

In use, frame 1 must first be adjusted to the table of the particular CT scanner with which the frame will be subsequently used to insure that the plane of the frame lies in the zero reference plane of the scanner. In order to perform this alignment, marker blocks 8-14 are placed on the frame with the cross hair markings facing towards the outside. Frame 1 is attached to plates 50 and 52 and then plate 50 is then affixed to CT scanner table 200 by means of the thumbwheel 53 and screw 55.

The scanner table and the attached frame are then moved into the scanner gantry area in the conventional manner so that the lead shot markers 20 in each of alignment arms 8-14 lie within the scanner's reference plane as indicated by impingement of the scanner's laser beam on the cross hairs of markers 8-14. The scanner is then operated to generate a lateral view with the gantry tilt equal to zero to check that frame is properly aligned. In this view, the marker lead shots show as darkened point images and proper alignment is indicated when a straight line can be passed through the four images and the line is perpendicular to the graduated baseline of the scanner. If a straight line cannot be passed through all images or the line is not perpendicular to the scanner baseline, an Allen wrench 61 is used to loosen the attachment screws 58 and 60 slightly so that frontplate 52 can be moved relative to backplate 50. Allen wrench 59 is then used to adjust adjustment set screws 170-176 to change the plane of frame 1 relative to the plane of scanner table 200.

After appropriate adjustments have been made, screws 58 and 60 are tightened to fix the position of the frame relative to the table and an additional lateral view is generated to verify that the plane of frame 1 is properly aligned to the table. After a lateral view indicates that a straight line passing through the marker shot images is perpendicular to the scanner baseline, the CT operator can adjust the position of the table so that the marker images lie in the scanner reference or "zero" plane.

After this latter adjustment has been made, an axial scan is taken in the scanner reference plane with a 1.5 mm thickness. The image of the resulting slice is examined to check that the images of the four marker shots lie on the axes of the CT grid which are superimposed on the scan image by the scanner electronics. If the marker images do not lie on the scanner grid axes, frame 1 must be rotated in its plane with respect to the scanner table. This rotation is performed by again loosening attachment screws 58 and 60. Set screws 170-176 are not moved in this adjustment. Instead, frame 1 is rotated slightly until the four marker images are superimposed on the grid.

Once the above alignment procedure has been completed there is no need to repeat the alignment when the frame is used with the same CT table provided that the relative positions of the table or the gantry are not disturbed. The frame may then be used to perform either brain biopsies or surgical operations.

In order to use frame 1 for a biopsy, the frame must first be affixed to the head of the patient. This may be done in the operating room, an anteroom or the CT scanner room. To allow the scanning of the entire head without interference between the images of the metal affixation pins and the CT brain image, the frame is affixed to the head as low as possible. To fix the frame it is initially centered on the head and the attachment screws are turned in until they just touch the scalp. At this point, the positions of the attachment pins are marked on the scalp with a marker. The frame is then removed and local anesthetic is injected into the scalp at the marked sites. The frame is then put back into position and the affixation screws are advanced to firmly attach the frame to the head.

Adapter 40 is attached to the table by means of thumbwheel 53, the patient is then placed on the CT table and frame is attached to adapter 40 by means of screws 54 and 56. Marker blocks 8-14 are then placed on the frame and the height of the table and the travel of the table are adjusted with the help of the CT laser beam and the cross hair markings on the marker blocks so that the laser beam strikes the alignment cross-hairs. When this position has been reached, due to the previous alignment procedure, the frame will be precisely aligned with the internal scanner coordinates.

The scanner table is then moved to the gantry and a lateral scout view of the head is taken to check the alignment of the frame with the zero reference plane of the scanner. Similarly, after ascertaining that the lateral alignment is correct, an axial scan at the reference plane is taken with a slice thickness of 1.5 mm to check the position of the marker images to be sure that they are precisely superimposed on the X and Y axes of the scanner.

After proper alignment is verified, the frame marker blocks are removed and the scanner is operated to take the number of scans necessary to identify the biopsy area.

At the CT scanner console, after the slice with the biopsy area is identified, a cursor can be moved to the biopsy location and the X and Y coordinates (computed by the scanner in a well-known manner) appear on the scanner screen (on the model 8800 CT scanner mentioned previously, the X and Y coordinate appear on the right lower corner of the screen. The Z coordinate appears on the left upper corner of the screen and is the distance that the slice is displaced from the zero plane). In accordance with the invention, due to the initial alignment procedure, these coordinates can be directly used to mechanically set the frame to guide the biopsy needle to the precise biopsy location.

After the X,Y and Z scanner coordinates have been ascertained, the patient and frame are disconnected from the CT table and transferred to an operating room where the frame is attached to a suitable headrest on the operating table which headrest holds the head immobile during the biopsy procedure.

To perform the biopsy, the patient is then prepped for a surgical operation in the conventional manner, and two graduated scale bars 70 and 71 (FIG. 1) are attached to frame 1 by means of four threaded fittings (only fittings 24 and 26 are shown in FIG. 1) and corresponding screws (such as screw 77). Each of these bars bears a scale (such as scale 73) which is graduated in the same divisions as the Y-axis scale of the CT scanner display. Due to the initial alignment, the Y coordinate number obtained from the scanner display can be directly correlated to this scale markings on bars 70 and 71.

A sliding attachment block 78 slides along a dovetail way 72 on bar 70 and can be fixed at any position by means of screws 76 or 80. Attachment block 78 contains an index line 79 which can be set opposite the desired Y-coordinate number on scale 73.

An additional graduated bar 75 is mounted on each side of the frame by sliding a dovetail way into the dovetail socket 74 of block 78. Bar 75 also bears a graduated scale (not shown in FIG. 1) on which the Z-coordinate number can be set. The Z-coordinate is determined by the location of the CT slice in which the image of the biopsy area occurs and may be set directly on the bar. After the Z-coordinate has been set, bar 75 is locked in place by means of set screw 76 which also locks the Y movement A bar similar to bar 75 is attached on the opposite side of frame 1.

A third set of bars (such as bar 84) are then mounted perpendicularly on the top of bar 75. Each of these bars also bear a graduated scale which corresponds to the scanner X-coordinate. A similar graduated bar is mounted on the opposite side of the frame.

With the graduated bars in place, the coordinates obtained from the scanner are transferred and set as mechanical adjustments on the respective bar scales. In order to set the depth of the biopsy needle, a centering rod 106 is mounted on arc 100 (centering rod 106 has a spring attachment which allows it to be easily removed and inserted). Mounted on arc 100 is a needle carrier 108 which consists of a slider 123 and a calibrated micrometer drive unit 112. In order to set the needle depth, the micrometer needle drive is first set to its "zero" point by turning knob 118 (which operates a rack-and-pinion gear arrangement) and then locked in position by tightening screw 116. A biopsy needle is placed in the drive unit 119 and positioned at a reasonable location where it is fixed by tightening screw 121. Allen wrench 110 is then used to loosen set screw 109 on needle or electrode carrier 108 to move micrometer drive unit 112 until the needle tip touches the center point on rod 106. Allen wrench 110 is then used to tighten set screw 109 to fasten carrier 108 in position. Slider 123 is then removed from arc 100 by loosening set screw 116. Centering rod 106 is also removed.

Arc 100 is subsequently mounted on frame 1 by placing pins 102 into holes 90 on bar 84 which, as previously described, has been attached to frame 1. The arc may be rotated about its axis using protractor 104 as a guide until the needle position is aligned with an existing burr hole, if any. At this point, the needle carrier 119 is remounted on the arc. Needle carrier 119 is then advanced to its zero point with the micrometer drive to position the needle point at the biopsy area. A biopsy sample is taken in the usual manner.

In order to use frame 1 for functional neurosurgery (for example, a thalamotomy), in accordance with the invention, each of the bars, such as bar 75, that are used for biopsy purposes are replaced with a dual post arrangement, 31. This arrangement comprises two bars, 130 and 132, which are graduated in the same manner as bar 75 to allow for Z-axis adjustment. At the top of each of bars 130 and 132 is mounted perpendicularly another small bar (one of bars 134 and 136, respectively) to allow for X-axis adjustment. Each of bars 134 and 136 bears a post and the top of each post is joined to the other post by a bridge piece 138.

Post 136 is joined by a pivot to bridge piece 138 and post 134 is joined to bridge piece 138 by a pin and slot arrangement. In use, rod 132 is aligned to the anterior commissure position and rod 130 is aligned to the posterior commissure location and thus the bridge portion 138 represents the anterior commissure-posterior commissure line (AC-PC line). The coordinates of the AC-PC line can be determined from the scanner using a midline sagittal reconstruction of the region of the third ventricle in the normal manner. Since the position of each of rods 130 and 132 and bridge piece 138 can be adjusted independently, the mechanism allows for compensation for the differing heights of the anterior commissure and the posterior commissures and a lateral misalignment of the anterior and posterior commissures.

Mounted on bridge 138, is an additional bar 140 which is used to set the transverse coordinate of the target relative to the mid-line of the patient's third ventricle. Bar 140 can slide over AC-PC bridge 138 (front and back) with attachment block 137 to set the anterior-posterior coordinate of the target. The level of the target above or below the AC-PC line can be set with block 142.

In order to use the apparatus for functional neurosurgery, the patient is taken to the CT room and the various scans are taken, as previously described, for a biopsy procedure so that the AC-PC line can be determined. In the operating room, dual-post bridge arrangements are attached to the lateral bars 70 on each side of the frame. The coordinates of the AC-PC line as determined from the CT scanner are set directly on the bars 130 and 132.

A convenient burr hole is then drilled in the skull and an appropriate lesion is made using a radio-frequency generator.

Although only one illustrative embodiment of the invention has been described, other embodiments within the spirit and scope of the invention will be immediately apparent to those skilled in the art.

What is claimed is:

1. In a stereotactic instrument for neurosurgery of the brain for use with a noninvasive scanner such as a CT scanner having a moveable table, said instrument having a rigid frame, means for attaching the frame to the patient's skull, means for determining scanner coordinates indicating a precise brain location from scanner measurements, means attached to said frame for defining a set of frame coordinates, and means attached to said frame for precisely guiding a surgical implement to said brain location in accordance with said scanner coordinates, the improvement comprising, means for releasably fastening said frame to said CT scanner table, and means for adjusting the plane of said frame to a predetermined position relative to the plane of said CT scanner table.

2. In a stereotactic instrument, the improvement according to claim 1, wherein the adjustment means comprises, means for adjusting the plane of the frame to be perpendicular to the plane of the table, and means for rotating the frame so that the frame coordinates can be aligned to a predetermined position relative to the scanner coordinates.

3. In a stereotactic instrument, the improvement according to claim 2, wherein the CT scanner has a zero reference plane and the predetermined position is the zero reference plane.

4. In a stereotactic instrument, the improvement according to claim 3 wherein the scanner coordinates are graduated in divisions and the means for defining frame coordinates is graduated in the same divisions as the scanner coordinates.

5. In a stereotactic neurosurgical instrument, the improvement according to claim 1 the adjusting means including means for rotating said frame relative to said table so that said frame coordinates can be aligned to a predetermined position relative to said scanner coordinates.

6. In a stereotactic neurosurgical instrument, the improvement according to claim 5, wherein said rotating means rotates said frame so that said frame coordinates coincide with said scanner coordinates.

7. In a stereotactic neurosurgical instrument, the improvement according to claim 1, wherein said adjusting means adjusts the plane of said frame to be perpendicular to the plane of said table.

8. In a stereotactic instrument for neurosurgery of the brain for use with a noninvasive scanner such as a CT scanner having a moveable table, said instrument having a rigid frame, means for attaching the frame to the patient's skull, means for determining scanner coordinates indicating a precise brain location from scanner measurements, means attached to said frame for defining a set of frame coordinates, and means attached to said frame for precisely guiding a surgical implement to said brain location in accordance with said scanner coordinates, the improvement comprising, a first attachment plate, means for rigidly attaching said first plate to said scanner table, a second attachment plate, means for rigidly attaching said second plate to said frame, means for moveably connecting said first plate to said second plate, means for adjusting the plane of said first plate relative to the plane of said second plate so that the plane of said frame can be adjusted to a predetermined position relative to the plane of said CT scanner table.

9. In a stereotactic neurosurgical instrument, the improvement according to claim 8, wherein said connecting means comprises an adjustable fastening means which fastening means can be loosened to allow relative movement between said first and second plate and tightened to lock said plates together.

10. In a stereotactic neurosurgical instrument, the improvement according to claim 8, wherein said adjusting means comprises at least one adjustment screw, said screw being threaded into said one of said plates and bearing against said other plate.

11. A stereotactic instrument for neurosurgery of the brain for use with a noninvasive scanner such as a CT scanner having a moveable table and means for determining scanner coordinates indicating a precise brain location, said instrument comprising, a rigid frame, means for attaching the frame to the patient's skull, means attached to said frame for defining a set of frame coordinates, means attached to said frame for precisely guiding a surgical implement to said brain location in accordance with said frame coordinates, a first attachment plate, means for rigidly attaching said first plate to said scanner table, a second attachment plate, means for rigidly attaching said second plate to said frame, means for moveably connecting said first plate to said second plate, means for adjusting the plane of said first plate relative to the plane of said second plate so that the plane of said frame can be adjusted to a predetermined position relative to the plane of said CT scanner table.

12. A stereotactic neurosurgical instrument according to claim 11, wherein said frame coordinate defining means further comprises, means attached to the frame for defining the AC-PC line of the brain from CT scanner coordinates while maintaining the frame in fixed position in relation to the skull, and means attached to the AC-PC defining means for adjusting the position of the means for guiding the surgical implement.

13. A stereotactic neurosurgical instrument according to claim 12 wherein the CT scanner defines X, Y and Z coordinates and the AC-PC defining means is characterized by
  means attached to the frame for defining a Y set of frame coordinates corresponding to the Y coordinates of the CT scanner,
  means attached to the Y coordinate means for defining a Z set of frame coordinates corresponding to the Z coordinates of the CT scanner
  means attached to the Z coordinate means for defining an X set of frame coordinates corresponding to the X coordinates of the CT scanner, and
  means corresponding to the AC-PC line and positionable by adjusting the X, Y and Z frame coordinate means.

14. A stereotactic neurosurgical instrument according to claim 13 wherein
  the Y coordinate means is characterized by a detachable graduate scalebar attached to the frame,
  the Z coordinate means is characterized by a first pair of graduated bars, each of the bars being connected perpendicularly to the scalebar and capable of independent movement laterally along the scalebar,
  the X coordinate means is characterized by a second pair of graduated bars attached perpendicularly to the first pair of graduated bars and capable of independent movement along the X axis, and
  the means corresponding to the AC-PC line is characterized by a bridge piece pivotably connecting the second pair of graduated bars.

15. In a stereotactic instrument, the improvement according to claim 11 wherein the CT scanner has a zero reference plane and the predetermine position is the zero reference plane.

16. In a stereotactic instrument, the improvement as claimed in claim 15 wherein the scanner coordinates are graduated in divisions and the means for defining frame coordinates is graduated in the same divisions as the scanner coordinates.

17. A stereotactic neurosurgical instrument according to claim 11, wherein said connecting means comprises a plurality of connecting screws, said screws being threaded into one of said plates, and said screws passing through oversized holes in said other plate so that said screws can be loosened to allow relative movement between said first and second plates and tightened to lock said plates together.

18. A stereotactic neurosurgical instrument according to claim 17, wherein said adjusting means comprises a plurality of adjustment screws, each of said plurality of screws being threaded into said one of said plates and bearing against said other plate.

19. A stereotactic neurosurgical instrument according to claim 18, wherein said adjustment screws are threaded into said one plate in a geometrical pattern.

20. A stereotactic neurosurgical instrument according to claim 19, wherein said pattern comprises a rectangle with said screws being threaded into said one plate at the corners of said rectangle.

21. A stereotactic neurosurgical instrument according to claim 20, wherein said means for rigidly attaching said first plate to said scanner table comprises a thumbwheel and a screw attached to said thumbwheel, said thumbwheel screw engaging a tapped hole in said table.

22. A stereotactic neurosurgical instrument according to claim 21, wherein said means for rigidly attaching said second plate to said frame comprises a plurality of brackets.

23. A stereotactic neurosurgical instrument according to claim 22, wherein said frame is square.

24. A stereotactic neurosurgical instrument according to claim 23, wherein said defining means comprises a plurality of marker posts, each of said posts containing a radio-opaque marker which generates a dot image on said scanner.

25. In a stereotactic instrument, the improvement as claimed in claim 24 wherein the CT scanner has a zero reference plane, the predetermined position is the zero reference plane and the plane of the frame is located in the zero reference plane by locating the dots in the zero reference plane.

26. In a stereotactic instrument, the improvement as claimed in claim 25 further comprising means for securing the frame to a headrest for immobilizing the patient's skull during surgical procedures.

27. In a stereotactic instrument, the improvement as claimed in claim 26 wherein the scanner coordinates are graduated in divisions and the means for defining frame coordinates is graduated in the same divisions as the scanner coordinates.

28. In a stereotactic instrument for neurosurgery of the brain, said instrument having a rigid frame, means for attaching the frame to the patient's skull, means for determining coordinates of a lesion areas of the brain, an arc attached to said frame for precisely guiding a surgical implement to said brain location in accordance with said frame coordinates, the improvement comprising,
  a surgical implement holder connected to said arc,
  said implement holder comprising,
    a graduated slider,
    means for removably attaching said slider to said arc,
    an implement carrier,
    means for slidably attaching said implement carrier to said slider, and
    a calibrated micrometer drive means for advancing said surgical implement a precise distance relative to said slider, whereby said carrier can be preset to a precise location relative to said slider and said slider together with said carrier can be removed from said arc during setup of said instrument prior to surgery and replaced for surgery while maintaining said preset location.

* * * * *